United States Patent [19]
Castagna

[11] Patent Number: 5,411,487
[45] Date of Patent: May 2, 1995

[54] HYPODERMIC SYRINGE WITH AUTOMATIC NEEDLE COVER

[76] Inventor: John F. Castagna, 200 W. Sarah St., Milford, Pa. 18337

[21] Appl. No.: 986,492

[22] Filed: Dec. 7, 1992

[51] Int. Cl.$^6$ ............................................. A61M 5/32
[52] U.S. Cl. ................................. 604/198; 604/263
[58] Field of Search ....................... 128/760, 763, 765; 206/364, 365, 363; 604/187, 192, 193, 194, 197, 198, 263

[56] References Cited

U.S. PATENT DOCUMENTS

| | | | |
|---|---|---|---|
| 4,900,311 | 2/1990 | Stern et al. | 604/263 X |
| 4,923,477 | 5/1990 | Morgan | 604/198 |
| 4,932,990 | 6/1990 | Walker et al. | 604/198 X |
| 4,943,282 | 7/1990 | Page et al. | 604/198 |
| 4,966,592 | 10/1990 | Burns et al. | 604/263 X |
| 5,135,510 | 8/1992 | Maszkiewicz et al. | 604/198 X |

Primary Examiner—Sam Rimell
Attorney, Agent, or Firm—Ostrolenk, Faber, Gerb & Soffen

[57] ABSTRACT

A hypodermic syringe comprises a cylindrical piston barrel, a piston plunger slidable in and extending out one end of the piston barrel, a rubber-like piston attached to one end of the piston plunger, a needle extending from the other end of the piston barrel, and a spring-loaded needle cover in the form of a cover tube slidable over the piston barrel. The cover tube includes a locking mechanism for locking the cover tube in an extended position over the needle or in a retracted position exposing the needle. The locking mechanism comprises an axial slot or keyway provided on the cover tube and having transverse projections at each end, a pin on the piston barrel adjacent to the needle end extending radially outwardly into the slot of the cover tube, and a spring positioned between the distal ends of the piston barrel and the cover tube. In the retracted position of the cover tube, the spring located inside the cover tube is compressed. When an injection is given, the cover tube is automatically unlocked and the compressed spring expands, pushing the cover tube over the needle. Once over the needle, the cover tube is locked in place. In operation the slot rides against the pin and guides the movement of the cover tube.

15 Claims, 2 Drawing Sheets

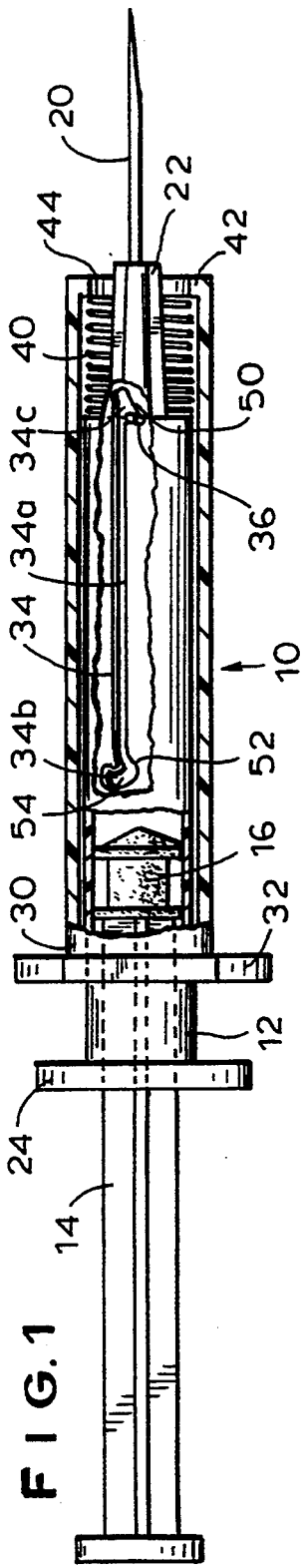
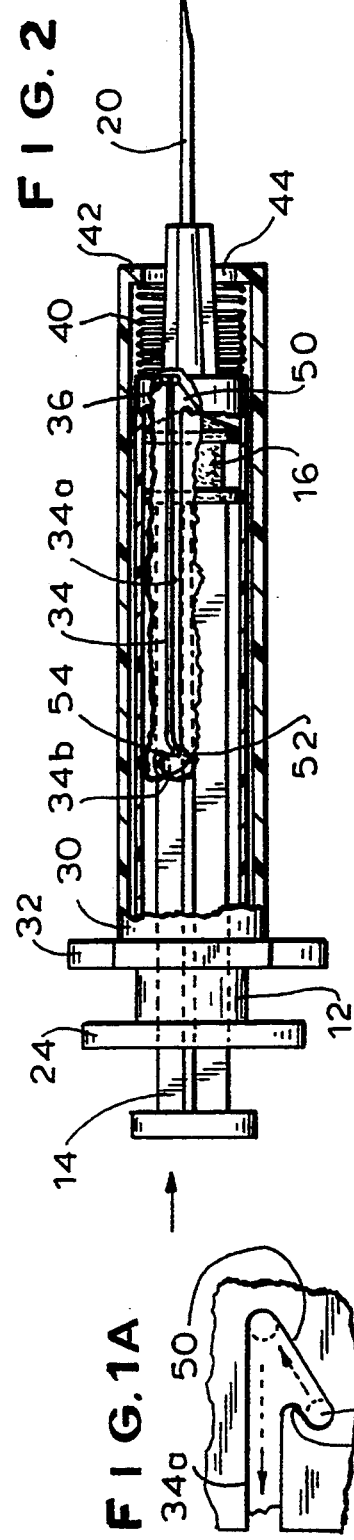
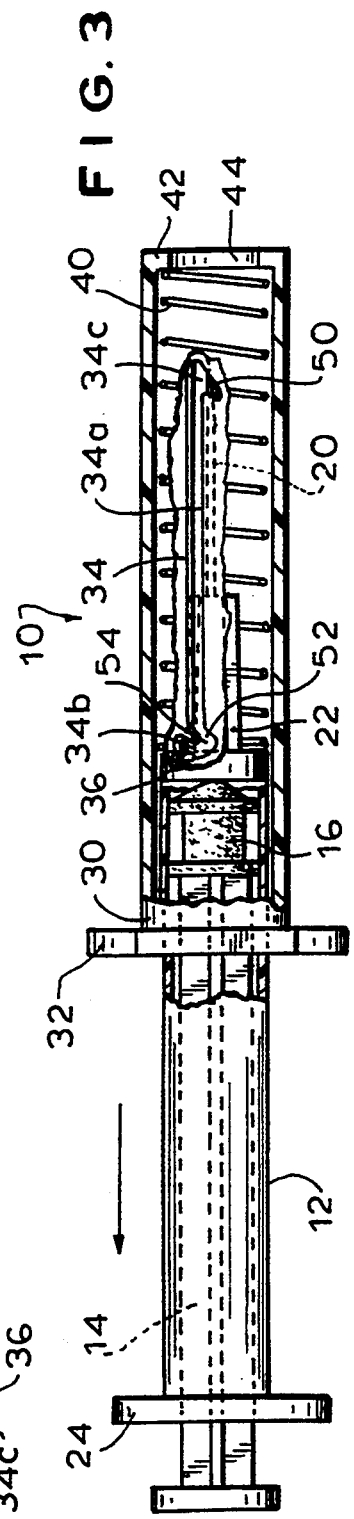

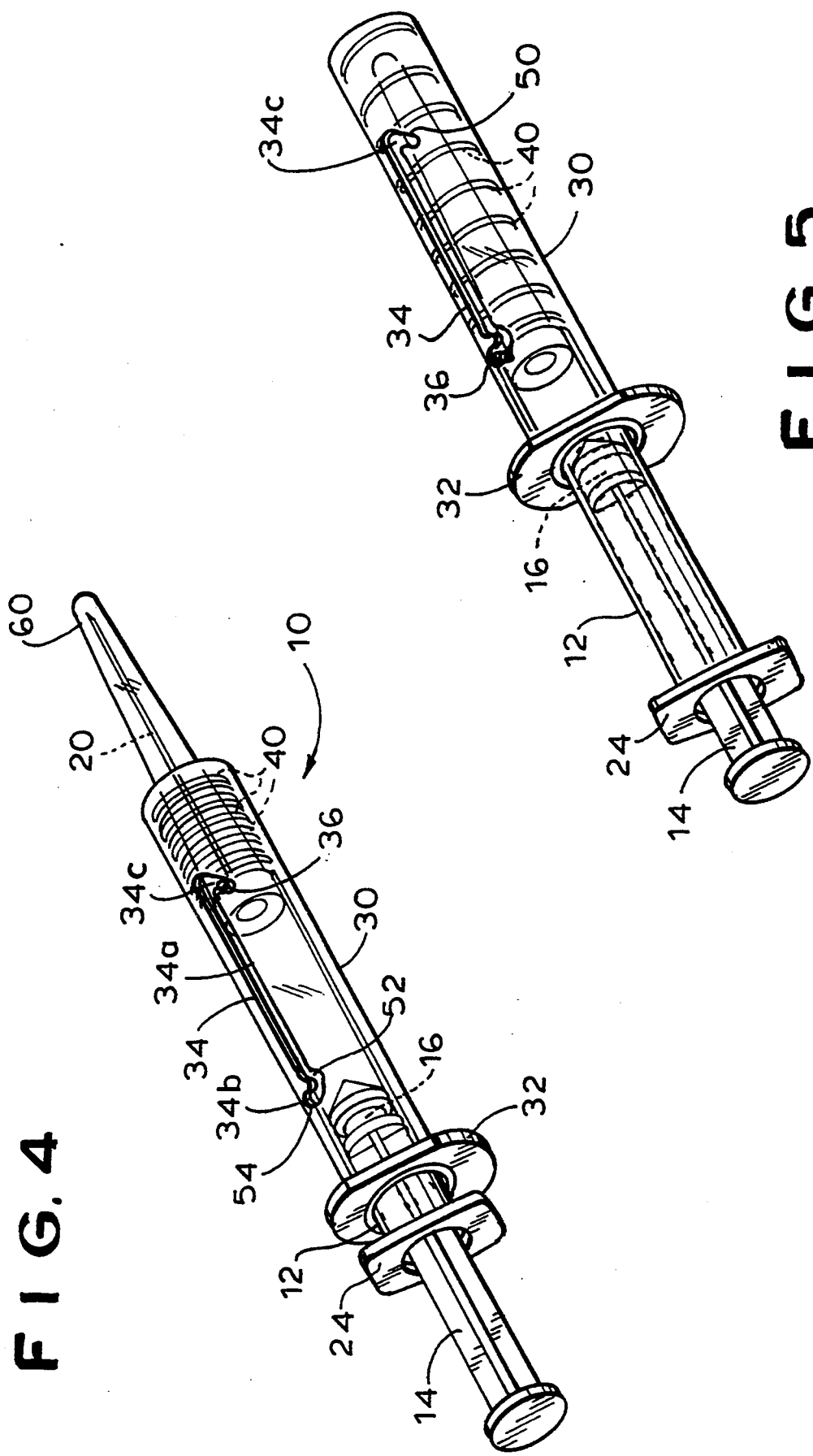

HYPODERMIC SYRINGE WITH AUTOMATIC NEEDLE COVER

BACKGROUND OF THE INVENTION

1. Field of the Invention

The present invention relates to hypodermic syringes. More specifically, the invention relates to hypodermic syringes with automatic needle covers.

2. Related Art

Syringes which are commonly in use do not have any mechanism to prevent infections caused by needlestick injuries. Many serious diseases, most notably Acquired Immune Deficiency Syndrome and hepatitis, can be spread by accidental needlestick after skin injections. Since health care workers frequently do not practice universal precautions because they lack the training or time, universal precautions cannot prevent transmission of HIV occupationally.

To reduce cross-infection risks of recapping the needle after injection for safe disposal, a pull-away self-capping syringe was designed. Following injection, the user pulls a protective plastic barrel back over the soiled needle. The hand slides away from the needle, rather than toward it. Once engaged, the pull-away system locks into place for safe needle disposal.

In order to provide better protection, a blunt plastic "cannula" was developed to replace conventional steel needles for a majority of needle applications, including peripheral and central line IV connections, Y-site access, and heparin lock therapy.

Despite the availability of new protective devices such as needleless IV connectors, little data exists to confirm injury reduction, ease of use, and effectiveness in patient care. The method of infection control still appears uncertain.

It is thus desirable that an automatic safety shield be built into conventional syringes to enable physicians and other health care workers to safely dispose of used syringes without causing a needlestick. Also, in many instances health care workers may accidently prick themselves, especially in cases of high trauma, if the needle is not automatically covered after an injection.

It is thus desirable that a safety shield be built into conventional syringes to enable physicians and other health care workers to safely administer injections and dispose of used syringes without changing the traditional injection techniques. It is to the solution of this and other problems to which the present invention is directed.

SUMMARY OF THE INVENTION

It is therefore a primary object of the present invention to provide a needle cover for a hypodermic syringe which automatically locks into place immediately after the completion of an injection.

It is another object of the invention to provide an automatic needle cover which can be used with a syringe without changing traditional injection techniques.

These and other objects of the invention are achieved by the provision of a hypodermic syringe which may comprise a cylindrical piston barrel, a piston plunger slidable in and extending out one end of the piston barrel, a rubber-like piston attached to one end of the piston plunger, a needle extending from the other end of the piston barrel, and a spring loaded needle cover in the form of a cover tube slidable over the piston barrel. The cover tube includes a locking means for locking the cover tube in an extended position over the needle or in a retracted position exposing the needle. In the retracted position of the cover tube, a spring located inside the cover tube is compressed. When an injection is given, the cover tube is automatically unlocked and the compressed spring expands, pushing the cover tube over the needle. Once over the needle, the cover tube is locked in place.

The cover may have an axial slot or keyway provided with transverse circumferential projections at each end. A pin on the piston barrel adjacent to the needle end extends radially outwardly into the slot of the cover tube. In operation the slot rides against the pin and guides the movement of the cover tube.

To release the cover tube from the retracted locked position, a small pressure is exerted on the cover tube in a direction back away from the needle. The back pressure forces the angled transverse portion of the slot to ride against the pin which then guides the pin back to the axial section of the slot. Once back pressure is released, the spring expands and forces the tube to travel with the pin moving along the axial section of the slot. At the other end of the slot the pin may be guided into a further transverse circumferential portion of the slot such that the cover tube is forced into a locked extended position.

BRIEF DESCRIPTION OF THE DRAWINGS

The invention will be better understood by reading the following Detailed Description of the Preferred Embodiment with reference to the accompanying drawing figures, in which like reference numerals refer to like elements throughout, and in which:

FIG. 1 is a cross-sectional view of the syringe with automatic needle cover according to the invention. The syringe is in position for the administration of an injection.

FIG. 1A is a diagrammatic view showing the relative path of travel of the needle cover over FIG. 1, during the administration of an injection.

FIG. 2 is a cross-sectional view of the syringe of FIG. 1, shown in the process of administering an injection.

FIG. 3 is a cross-sectional view of the syringe of FIG. 1, in position following completion of the administration of an injection.

FIG. 4 is a perspective view of the syringe of FIG. 1, in position prior to the administration of an injection.

FIG. 5 is a perspective view of the syringe of FIG. 1, in position following completion of the administration of an injection.

DETAILED DESCRIPTION OF THE PREFERRED EMBODIMENT

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

Referring now to FIGS. 1-5, there is shown a hypodermic syringe 10 having a proximal end (the left end in all drawing figures) and a distal end (the right end in all figures). Hypodermic syringe 10 comprises a cylindrical piston barrel 12 having a conventional piston plunger 14 slidable in and extending out one end of piston barrel 12.

A rubber-like piston 16 is attached to the distal end of piston plunger 14 for slidable movement in piston barrel 12 in mating contact with the inner surface of piston barrel 12, while a needle 20 extends from the proximal end of piston barrel 12. The distal end of piston barrel 12 is undercut in a conventional manner at 22, while the proximal end of piston barrel 12 is conventionally provided with a radially-extending flange 24. A spring-loaded needle cover in the form of a cover tube 30 is slidable over piston barrel 12.

Cover tube 30 has a flange 32 extending radially outwardly from its proximal end, for a purpose to be described hereinafter. Cover tube 30 also has an axial slot or keyway 34 having a straight section 34a provided with proximal and distal transverse projections or branches 34b and 34c at its proximal and distal ends, respectively. A pin 36 on piston barrel 12 adjacent to needle 20 extends radially outwardly into slot 34 of cover tube 30. In operation slot 34 rides against pin 36 and guides the movement of cover tube 30.

A coil spring 40 is positioned between the distal end of piston barrel 12 and the distal end of cover tube 30. The distal end of cover tube 30 has a small, inwardly-extending lip 42 to retain one end of spring 40. The other end of spring 40 is friction fitted to the undercut distal end of piston barrel 12. Lip 42 defines an aperture 44, through which needle 20 and the distal end of piston barrel 12 can extend when cover tube 30 is in the retracted position.

Straight section 34a of slot 34 and projections 34b and 34c in combination with pin 36 and spring 40 comprise a locking means for locking cover tube 30 in an extended position over needle 20 or in a retracted position exposing needle 20. In the retracted position of cover tube 30, spring 40 is compressed. When an injection is made, cover tube 30 is automatically unlocked and the compressed spring 40 expands, pushing cover tube 30 over needle 20. Once over needle 20, cover tube 30 is locked in place.

The friction between spring 40 and distal end of piston barrel 12 prevents spring 40 from rotating easily. Spring 40 also has some contact friction with lip 42 of cover tube 30. As a result, twisting cover tube 30 in either direction tends to return cover tube 30 to the rest position of spring 40. Straight section 34a of the tube slot 34 is aligned with the rest position of spring 40.

In the retracted position of cover tube 30, spring 40 is compressed. Projection 34c at the distal end of slot 34 has a return angle portion 50 that extends back a short distance. To lock cover tube 30 in the retracted position, cover tube 30 must be slightly twisted in the direction of the return angle and then released. The compressed spring 40 expands, pushing cover tube 30 forward and locking it in projection 34c.

To release cover tube 30 from the retracted locked position, a small pressure is exerted on cover tube 30 in a direction back away from needle 20, for example by placing the fingers on the distal side of flange 32 while pressing the thumb on plunger 14 to give an injection. The back pressure forces return angle portion 50 of slot 34 to ride against pin 36, which then guides cover tube 30 back to straight section 34a of slot 34, as shown by the arrows in FIG. 1A. Once back pressure is released, spring 40 expands and forces cover tube 30 to travel along straight section 34a of slot 34. At the other end of slot 34, cover tube 30 is forced into a locked extended position at proximal projection 34b.

At proximal projection 34b, cover tube 30 is forced by the expansion of spring 40 to twist through angled portion 52 of proximal projection 34b and to twist back into a recessed or transverse area 54. Once pin 36 is in recessed area 54, cover tube 30 is locked in the extended position. Cover tube 30 is forced into recessed area 54 by the action of spring 40 which returns cover tube 30 to the rest position of spring 40.

In the extended position of cover tube 30, projection 34b at the proximal end of straight section 34a of slot 34 angles away for a short distance in one direction from straight section 34a and beyond the angled portion 52 returns in the opposite direction into a recessed area 54. Recessed area 54 is shaped to lock cover tube 30 in place.

To release cover tube 30 from the extended locked position and place it in the retracted position, cover tube 30 must be twisted manually in a direction that returns cover tube 30 back to straight section 34a of slot 34. Then cover tube 30 is pushed back until it locks in the retracted position, with the pin 36 in the projection 34c, as previously described.

In practice, hypodermic syringe 10 can be supplied with cover tube 30 in the retracted or extended position. At the discretion of the supplier, syringe 10 can also have a protective needle cap 60. When preparing to make an injection, cover tube 30 is placed in the retracted position and the protective needle cap 60 removed. Under normal practice, air is drawn into piston barrel 12 and expelled into a closed vial (not shown) of the liquid to be injected. In order to prevent cover tube 30 from being released from the retracted position, syringe 10 is held at the proximal end of piston barrel 12 at flange 24 while the injection is being prepared.

The vial usually has a rubber-like stopper. Needle 20 is pushed through the stopper and air is forced into the vial and then liquid is drawn into piston barrel 12. Needle 20 is then injected into the skin. During the injection part of the procedure, syringe 10 is used in a conventional manner, except that the fingers are placed on the distal side of flange 32 of cover tube 30 as plunger 14 is depressed.

As plunger 14 is pushed into piston barrel 12 to expel the liquid, a force is developed between plunger 14 and cover tube 30. This force which is back away from needle 20 unlocks cover tube 30 as previously described. When the injection is completed and needle 20 is withdrawn and laid down, cover tube 30 by spring action automatically covers needle 20 and locks in the extended position, also as previously described.

During the unlocking of cover tube 30, piston barrel 12 twists slightly. This twisting is imperceptible to the operator of the syringe, because the rubber-like piston 16 is very loosely coupled to plunger 14. As a result when piston barrel 12 twists, the twisting is not transmitted to plunger 14 or cover tube 30.

All components of syringe 10 are made using materials conventionally used for syringe components and are easily moldable by ordinary techniques. It is contemplated that piston barrel 12, piston plunger 14, and tube cover 30 can, for example, be made using polystyrene, acrylic, nylon, or any other plastic material which will not interact with the fluid to be drawn into cylinder barrel 12, and which will meet the strength, temperature, humidity and other requirements for syringe components.

Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically described.

What is claimed is:

1. A hypodermic syringe comprising:
   a piston barrel having proximal and distal ends, a needle mounted on said distal end, and an axially extending cavity defined by an inner surface;
   a piston plunger having proximal and distal ends, said distal end facing said needle and said proximal end being positioned externally of said piston barrel;
   a piston mounted on said distal end of said piston plunger for slidable movement in said piston barrel in mating contact with said inner surface of said piston barrel between an inserted position and a withdrawn position; and
   a cover tube having a distal end and a proximal end and an inner surface defining a cavity, said cover tube being axially movable between an extended position in which said cover tube extends over and fully covers said needle and a retracted position in which said cover tube is positioned over said piston barrel and said needle extends outwardly from said tubular cavity; and
   a locking arrangement for selectively locking said cover tube in said retracted position,
   said locking arrangement including means for automatically releasing said cover tube from said retracted position upon the application of back pressure to the cover tube, permitting said cover tube to move to said extended position when said hypodermic syringe is used to give an injection.

2. The syringe of claim 1, wherein said locking arrangement includes:
   a guide formed in said cover tube, said guide having a generally axial section and proximal and distal transverse branches respectively at opposite proximal and distal parts of said axial section; and
   an engaging device at said distal end of said piston barrel and engaging said guide for guiding movement of said cover tube along the length of said guide from one to the other of said branches.

3. The syringe of claim 2, wherein said syringe additionally includes biasing means for normally biasing said cover tube toward said extended position.

4. A hypodermic syringe comprising:
   a cylindrical piston barrel having proximal and distal ends, a needle mounted on said distal end, and an axially extending cylindrical cavity defined by an inner surface;
   a piston plunger having proximal and distal ends, said distal end facing said needle and said proximal end being positioned externally of said piston barrel;
   a piston mounted on said distal end of said piston plunger for slidable movement in said piston barrel in mating contact with said inner surface of said piston barrel between an inserted position and a withdrawn position; and
   a cover tube having a distal end and a proximal end and an inner surface defining a tubular cavity, said cover tube being axially movable between an extended position in which said cover tube extends over and fully covers said needle and a retracted position in which said cover tube is positioned over said piston barrel and said needle extends outwardly from said tubular cavity;
   locking means for selectively locking said cover tube in either said extended position or said retracted position, and biasing means for normally biasing said cover tube toward said extended position;
   wherein said locking means comprises:
   an axially-extending slot formed in said cover tube, said slot having a straight section and proximal and distal circumferential projections respectively at opposite proximal and distal ends of said straight section; and
   a pin extending radially outwardly from said distal end of said piston barrel and positioned in said slot for guiding movement of said cover tube along the length of said slot from one to the other of said projections:
   said proximal projection including an angled portion and a recessed area for automatically guiding said pin into said recessed area in said proximal projection when said cover tube is moved into said extended position, and permitting said pin to be released from said proximal projection for movement into said straight portion of said slot only by a slight manual rotation of said cover tube relative to said piston barrel; and
   said distal projection including an angled return portion defining an angle from said straight section toward said proximal end for automatically retaining said pin in said distal projection when the cover tube is in its retracted position, while automatically guiding said pin from said distal projection into said straight section of said slot in response to a slight relative movement of said piston barrel and said cover tube toward each other, so as to permit said cover to move toward said extended position.

5. A hypodermic syringe comprising:
   a cylindrical piston barrel having proximal and distal ends, a needle mounted on said distal end, and an axially extending cylindrical cavity defined by an inner surface;
   a piston plunger having proximal and distal ends, said distal end facing said needle and said proximal end being positioned externally of said piston barrel;
   a piston mounted on said distal end of said piston plunger for slidable movement in said piston barrel in mating contact with said inner surface of said piston barrel between an inserted position and a withdrawn position; and
   a cover tube having a distal end and a proximal end and an inner surface defining a tubular cavity, said cover tube being axially movable between an extended position in which said cover tube extends over and fully covers said needle and a retracted position in which said cover tube is positioned over said piston barrel and said needle extends outwardly from said tubular cavity;
   locking means for selectively locking said cover tube in either said extended position or said retracted position, and biasing means for normally biasing said cover tube toward said extended position;
   wherein said locking means comprises:
   an axially-extending slot formed in said cover tube, said slot having a straight section and proximal and distal circumferential projections respectively at opposite proximal and distal ends of said straight section; and
   a pin extending radially outwardly from said distal end of said piston barrel and positioned in said slot for guiding movement of said cover tube along the length of said slot from one to the other of said projections;

said distal projection including an angled return portion defining an angle from said straight section toward said proximal end for automatically retaining said pin in said distal projection when the cover tube is in its retracted position, while automatically guiding said pin from said distal projection into said straight section of said slot in response to a slight relative movement of said piston barrel and said cover tube toward each other, so as to permit said cover to move toward said extended position.

6. The syringe of claim 3, wherein said biasing means comprises a coil spring inside said cover tube and having a first end engaging said distal end of said cover tube and a second end bearing against said distal end of said cylinder barrel.

7. The syringe of claim 6, wherein said coil spring engages said cover tube and piston barrel so as to urge said cover tube to rotate about said piston barrel in a first sense for guiding said engaging device out of said distal branch and into said axial section of said guide.

8. The syringe of claim 7, wherein said engaging device moves in a second sense opposite to said first sense, relative to said cover tube, as it moves from said distal branch to said axial section.

9. The syringe of claim 8, wherein said proximal branch extends in said second sense from said axial section.

10. The syringe of claim 9, wherein said proximal branch has a transitional portion which extends in said first sense, and which interconnects said axial section with a portion of said proximal branch extending in said second sense.

11. The syringe of claim 3, wherein said distal branch has a return portion extending in a generally proximal direction and defining an angle from said axial section, the engaging device being urged into said return portion by said biasing means.

12. The syringe of claim 2, wherein said locking arrangement further selectively retains said engaging device in said distal branch so as to lock said cover in said retracted position.

13. The syringe of claim 12, wherein said distal branch includes a return portion which defines an angle from said axial section and generally toward said proximal end.

14. The syringe of claim 13, wherein said syringe further includes biasing means for biasing said cover tube toward said extended position.

15. The syringe of claim 14, wherein the engaging device can be urged into said return portion by said biasing means so as to be retained in said return portion with the cover in said retracted position, and can be moved out of said return position by a slight relative movement of said piston barrel and cover tube toward each other, when the syringe is used to give an injection, so as to automatically release said cover tube from said retracted position and permit said cover tube to be urged by said biasing means into said extended position.

* * * * *